United States Patent
Motoyoshi et al.

(10) Patent No.: US 9,228,930 B2
(45) Date of Patent: Jan. 5, 2016

(54) OSCILLATING TYPE PHYSICAL PROPERTY MEASURING APPARATUS AND METHOD

(71) Applicant: RION Co., Ltd., Tokyo (JP)

(72) Inventors: Junichi Motoyoshi, Tokyo (JP); Takashi Iwakura, Tokyo (JP)

(73) Assignee: RION Co., Ltd., Tokyo (JP)

(*) Notice: Subject to any disclaimer, the term of this patent is extended or adjusted under 35 U.S.C. 154(b) by 0 days.

(21) Appl. No.: 14/357,119

(22) PCT Filed: Nov. 16, 2012

(86) PCT No.: PCT/JP2012/079787
§ 371 (c)(1),
(2) Date: May 8, 2014

(87) PCT Pub. No.: WO2013/080813
PCT Pub. Date: Jun. 6, 2013

(65) Prior Publication Data
US 2015/0233808 A1    Aug. 20, 2015

(30) Foreign Application Priority Data

Nov. 28, 2011    (JP) ................. 2011-258763

(51) Int. Cl.
*G01N 29/00*    (2006.01)
*G01N 11/16*    (2006.01)
*G01N 9/00*    (2006.01)

(52) U.S. Cl.
CPC ............... *G01N 11/16* (2013.01); *G01N 9/002* (2013.01)

(58) Field of Classification Search
CPC ...... G01F 1/3227; G01H 13/00; G01L 21/22; H03B 5/30; G01N 9/002
See application file for complete search history.

(56) References Cited

U.S. PATENT DOCUMENTS

| | | | |
|---|---|---|---|
| 3,382,706 A | 5/1968 | Matusik | |
| 4,114,423 A * | 9/1978 | Wenger | 73/24.05 |
| 4,177,669 A * | 12/1979 | Wenger | 73/32 A |
| 4,754,640 A | 7/1988 | Fitzgerald | |
| 5,054,313 A | 10/1991 | Fitzgerald | |
| 5,533,381 A * | 7/1996 | Seale | 73/19.03 |

(Continued)

FOREIGN PATENT DOCUMENTS

EP    0112156 A2    6/1984
EP    2128596 A2    12/2009
(Continued)

OTHER PUBLICATIONS

Landau, L. D. et al., "Fluid Mechanics", Second Edition, Course of Theoretical Physics, vol. 6, Institute of Physical Problems, U.S.S.R. Academy of Sciences, 1987, Pergamon Books Ltd.

(Continued)

*Primary Examiner* — Elias Desta
(74) *Attorney, Agent, or Firm* — Rankin, Hill & Clark LLP (57) ABSTRACT

An apparatus that is able to measure a viscosity and a density directly within a short time with a small amount of sample, which has been difficult for existing vibratory viscometer. The end part of an oscillator is formed in a shape, such as a sphere, whose resistance by a fluid can be logically derived, and the viscosity and the density of a fluid are calculated based on a predefined mechanical impedance and on an amplitude ratio and a phase difference of accelerations in the cases the oscillator is in the air and is in the fluid.

10 Claims, 3 Drawing Sheets

(56) References Cited

U.S. PATENT DOCUMENTS

| | | |
|---|---|---|
| 6,112,581 A | 9/2000 | Scheider et al. |
| 6,327,915 B1 * | 12/2001 | Van Cleve et al. ....... 73/861.357 |

FOREIGN PATENT DOCUMENTS

| | | |
|---|---|---|
| JP | 57135337 A2 | 8/1982 |
| JP | 07-181121 | 7/1995 |
| JP | 07-294408 | 11/1995 |
| JP | 11-173968 | 7/1999 |
| JP | 11-218481 | 8/1999 |
| JP | 2001-516060 | 9/2001 |
| JP | 2006-214842 | 8/2006 |
| JP | 2009-281801 | 12/2009 |
| JP | 2011-027653 | 2/2011 |
| WO | 99/13389 | 3/1999 |

OTHER PUBLICATIONS

International Search Report dated Dec. 18, 2012 filed in PCT/JP2012/079787.

German Office Action issued on Oct. 31, 2014 for the corresponding German Patent Application No. 112012004953.5; English translation of pp. 4-5.

* cited by examiner

OSCILLATING TYPE PHYSICAL PROPERTY MEASURING APPARATUS AND METHOD

TECHNICAL FIELD

The present invention relates to an oscillating type physical property measuring apparatus and method. In particular, the present invention relates to the oscillating type physical property measuring apparatus and the method thereof that is able to measure a viscosity, a density, and the like of a fluid using a small amount of sample within a short time.

BACKGROUND ART

In the viscosity measuring system of a fluid such as liquid, there are capillary viscometers, falling ball viscometers, rotational viscometers, vibratory viscometers, and so on. Among these viscometers, the vibratory viscometers have many advantages such as a continuous measuring ability allowed by the quick response, a wide dynamic range, a capability of the measurement even with a small amount of the fluid, an easy operation, and a capability of the measurement even during the fluid flowing.

Because of above advantages, the vibratory viscometers have been widely used for measuring the viscosity of the fluid. The technical concept disclosed by Patent Document 1 is featured in that a tuning fork is used for cancelling the reaction by the oscillation of the oscillator. Since the oscillator is a flat plate, however, the real part and the imaginary part of the resistance affecting on the oscillator are of the same value. Therefore, a measured value can be obtained only by the product of the viscosity and the density. Thus, in order to obtain the viscosity, it is necessary to know the density in advance or to divide the above measured value by the density that has been separately measured by a density meter.

Patent Document 2 discloses that the characteristic oscillation period is measured by vibrating a measurement cell in which a sample fluid is filled, and that the density of the measured sample is calculated from the known densities of the pure water and the air. In this method, the sample fluid is required to be filled in the measurement cell, which makes the inline measurement difficult.

CITATION LIST

Patent Documents

Patent Document 1: JP-A-2006-214842
Patent Document 2: JP-A-2011-027653

SUMMARY OF INVENTION

Problems to be Solved by the Invention

The purpose of the present invention is to solve each of the above-described problems that have been difficult to be solved by the conventional oscillating type viscometer. One of the objects of this invention is to provide an apparatus and a method that is able to directly measure the viscosity or the density within a short time using a small amount of sample. Further other object of this invention is to provide an apparatus and a method that allow for the inline measurement in a manufacturing line of a fluid product.

Further, other object of this invention is to provide an apparatus and a method that are able to simultaneously measure the viscosity and the density.

Solutions to the Problems

In order to achieve the above objects, the oscillating type physical property measuring apparatus according to one embodiment of this invention is configured with a probe inserted in a sample fluid and a signal processing unit. The probe is configured with an oscillator having a spherical oscillator end part as an example at the end of a sufficiently thin suspension rod that oscillates in the fluid, an oscillation driving unit of an electro-dynamic actuator and a piezoelectric sensor connected to the suspension rod.

An oscillation driving signal is transmitted from the main unit to the oscillator. On the other hand, the signal processing unit of the main unit receives an acceleration signal and a temperature signal of the oscillator and carries out various calculations to output the viscosity and the density.

The end part of the oscillator is shaped as the suitable shape like a sphere whose resistance affected by the sample fluid can be logically derived, and the viscosity and the density are calculated based on the predefined mechanical impedance of the probe, and on the amplitude ratio and the phase difference between a driving force and acceleration information, velocity information, or displacement information of the oscillator in the air obtained before the oscillator is put into the sample fluid and a driving force and acceleration information or velocity information, or displacement information obtained when the oscillator is inserted in the sample fluid.

Further, it has the means for correcting the influence to the suspension rod which supports the end part of oscillator by the mechanical impedance of the sample fluid. This allows more accurate measurement.

The oscillator suspension rod and a support part supporting the oscillator are coupled by a first elastic member that is a flat spring as an example, and the support part and a probe case are coupled by a second elastic member that is a flat spring as an example. Then, the stiffness of the second elastic member is sufficiently small so that the mechanical impedance of the probe case or a probe holder can be ignored. This allows to suppress the influence of the change in the holding condition by the probe holder and thus allows the measurer to hold the probe holder by hand in the measurement.

Further, in order to solve the above-described problems, the oscillating type physical property measuring method according to one embodiment of this invention, with using an oscillating type physical property measuring apparatus having an oscillator, has the features of detecting a driving force of an oscillation driving unit for oscillating the oscillation and information of acceleration, velocity or displacement of the oscillation, and of calculating the viscosity and/or the density of the fluid based on the predefined mechanical impedance and based on the amplitude ratio and the phase difference between oscillation velocity information or acceleration information or displacement information in the air obtained before the oscillator is put into the sample fluid and oscillation velocity information or acceleration information or displacement information obtained when the oscillator is inserted in the sample fluid.

Effects of the Invention

As described above, the oscillating type physical property measuring apparatus according to this invention is able to separately and simultaneously measure the viscosity and the density of the sample fluid. Therefore, the oscillating type physical property measuring apparatus according to this invention can be used not only as a viscometer of a fluid such as liquid, but also as a density meter or a kinematic viscometer and, further, as a hydrometer.

Further, it can have a function of obtaining the ratio of volume elasticity or of compressibility of the sample fluid, provided that the sonic velocity of the sample fluid can be obtained previously.

Additionally, the measurement can be carried out with immersing the probe end in the sample fluid. Thus, it is not always necessary to collect samples and it makes the inline measurement possible.

The small end part of the oscillator allows for the measurement with a small amount of the sample fluid. Also, the probe structure is simple. Furthermore, handheld measurement is possible because the influence affected from the holding condition by hand is just a little.

DESCRIPTION OF EMBODIMENTS

Figure 1:
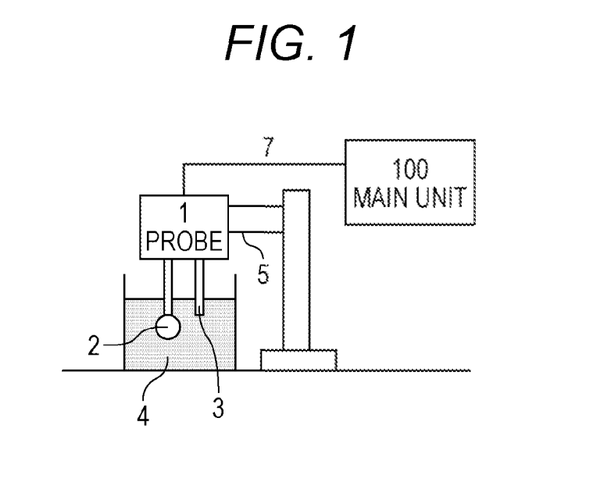
FIG. 1 is a configuration drawing of the oscillating type physical property measuring apparatus according to one embodiment of this invention.

Following description is the details of an embodiment of the oscillating type physical property measuring apparatus of this invention. FIG. 1 illustrates an outline of an embodiment of the oscillating type physical property measuring apparatus of this invention. An oscillator 2 and a temperature sensor 3 of a probe 1 held by a probe holder 5 is inserted into a sample fluid 4. The probe 1 is connected to a main unit 100 by a cable 7. The sample fluid 4 may be water, liquid condiment, liquid medicine, liquid detergent, oil, and ink, as examples.

Figure 2:
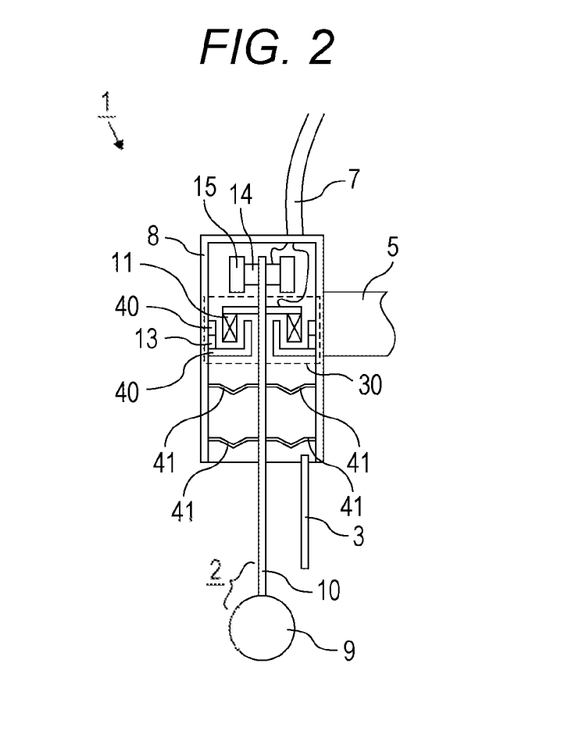
FIG. 2 is a structure drawing of a probe of the oscillating type physical property measuring apparatus according to one embodiment of this invention.

FIG. 2 illustrates an example of the structure of the probe 1. The oscillator 2 including a spherical oscillator end part 9 and a suspension rod 10 is designed inside of a probe case 8 held by the probe holder 5. The oscillator 2 is arranged with a driving unit 30 for providing oscillation to the oscillator 2 and with a piezoelectric sensor 14 for detecting the oscillation information of the oscillator 2. In order to provide a distortion to the piezoelectric sensor 14, a piezoelectric sensor mass 15 is arranged in the probe case 8. The temperature sensor 3 is arranged to the probe case 8. The piezoelectric sensor 14 and the temperature sensor 3 are electrically connected to the main unit 100 via the cable 7.

A magnet 13 configures a magnetic circuit together with a yoke 40 and is fixed to the probe case 8. Further, a coil 11 is fixed to the oscillator. The suspension rod 10 of the oscillator 2 and the probe case 8 are connected by an elastic member 41 that is a metal flat spring. The elastic member 41 has elasticity in the oscillating direction of the oscillator 2. On the other hand, the elastic member 41 is sufficiently stiff in the vertical direction against the oscillating direction. The resonance frequency of the oscillation is determined by the elastic member 41 and so on. That is, the oscillator 2 with the piezoelectric sensor 14 and the coil 11 has a structure so as to be suspended in the probe case 8 by the elastic member 41. The magnet 13, the yoke 40 and the coil 11 configure the driving unit 30 for providing oscillation to the oscillator 2. The oscillator 2 provides a simple harmonic oscillation in the direction of the center axis of the suspension rod 10.

The above-described structure of the probe 1 is an example of this invention. In the above description, the example of the spherical oscillator end part 9 is described as an example. However, the shape of the oscillator end part 9 is not limited to it. The oscillator end part 9 may have various shapes as long as the resistance affected thereto by the sample fluid can be logically calculated, such as a shape that a hemisphere is provided to each of both ends of a cylinder vibrated in the direction of the center axis of the cylinder. All of these shapes are encompassed in the technical concept of this invention.

Figure 3:
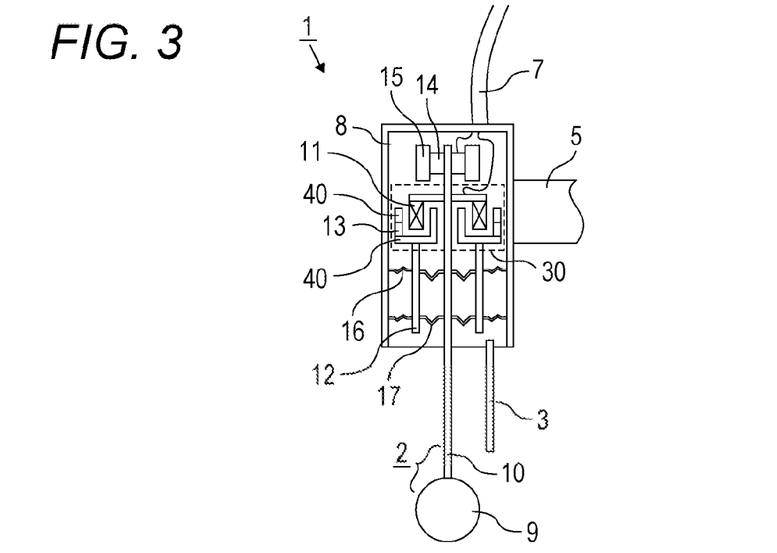
FIG. 3 is a structure drawing of a probe of the oscillating type physical property measuring apparatus according to another embodiment of this invention.

As illustrated in FIG. 3, in the probe 1, a first elastic member 17 may be arranged to the probe case 8 via a support part 12 and a second elastic member 16. Further, the magnetic circuit configured by the magnet 13 and the yoke 40 may be arranged to the support part 2 instead of the probe case 8. The first elastic member 17 and the second elastic member 16 are metal flat springs and transformed with elasticity so that the oscillator 2 moves in the oscillating direction. On the other hand, the first elastic member 17 and the second elastic member 16 are hardly transformed in the vertical direction to the oscillating direction. Further, the use of the second elastic member 16 can make to suppress the influence from the change in the holding condition of the case 8 by the probe holder 5. With suppressing the influence from the change in the holding condition, the measurement can be done with the probe 1 being held by the hand.

In this example, the structure that the oscillator makes a simple harmonic oscillation with impressing the alternating current to the coil 11 is mentioned. However, the method of driving the oscillator may be available with an electromechanical converter other than the electro-dynamic type. Further, the oscillator is inserted in the vertical direction to the liquid surface. In the case where the oscillator is inserted from obliquely direction or horizontal direction and oscillates, however, calibration can be done according to such situations.

It is noted that the material of the oscillator 2 should be metal such as stainless which avoids rust. The diameter of the suspension rod 10 of the oscillator 2 should desirably be sufficiently small and approximately equal to or less than one-fifth of the diameter of sphere as the oscillator end part 9. The diameter of the oscillator end part 9 is approximately 1 mm to 1 cm. For this example, it is 3 mm.

The resonance frequency in the condition where the oscillator 2 is not immersed in the sample fluid 4 (in the air) is substantially determined by the spring coefficient of the first elastic member 17, the mass of the oscillator 2, the mass of the piezoelectric sensor mass 15 and the coil 11 of the electro-dynamic driving unit and the mass of the support part 12 including the magnet 13 and the yoke 40. For this example, the probe of the structure of FIG. 3 is used.

Figure 4:
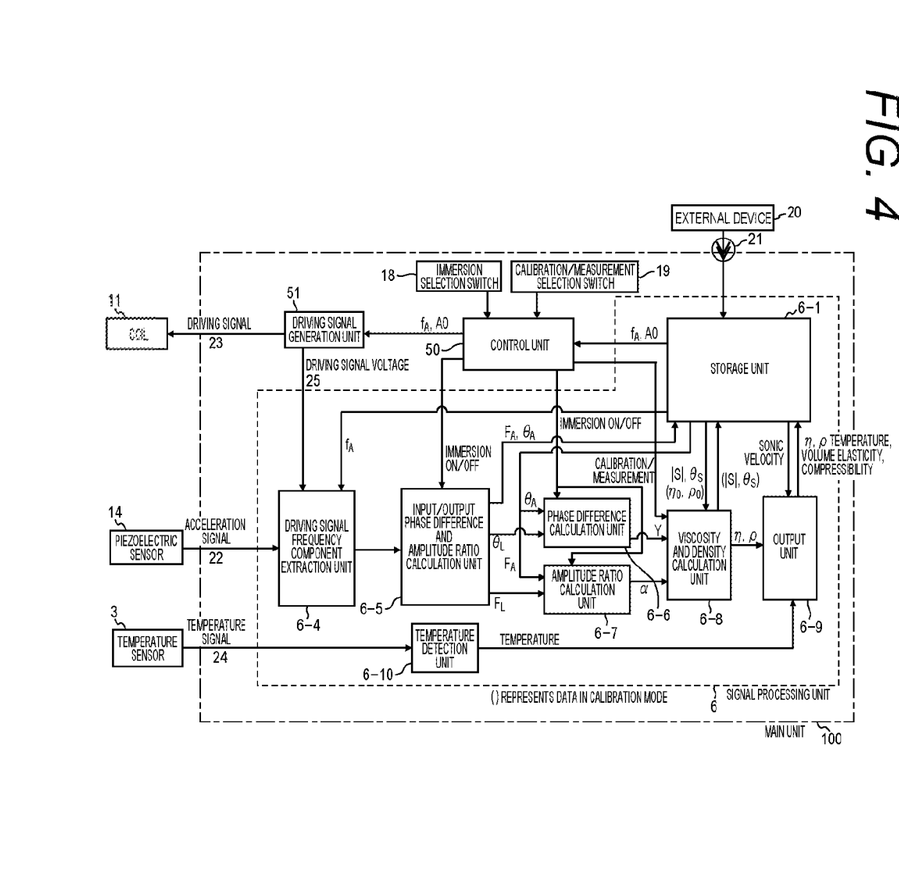
FIG. 4 is a block diagram of a signal processing unit of the oscillating type physical property measuring apparatus according to one embodiment of this invention.

Next, the main unit 100 is described with using the structure of FIG. 4. A control unit 50 picks up a driving signal frequency $f_A$ and a driving signal amplitude $A_0$ of the driving signal from a storage unit 6-1 and transmits it to a driving signal generation unit 51. From the driving signal generation unit 51, a driving signal 23 for making oscillation and driving the oscillator 2 is transmitted to the coil 11. The driving signal generation unit 51 is configured with a constant current driving circuit. The driving signal generation unit 51 provides substantial constant driving current, which is less affected from the fluctuation by the load, to the coil 11. The voltage proportional to the driving current mentioned above is outputted from the driving signal generation unit 51 as a driving signal voltage 25.

The output signals from the probe 1 are an acceleration signal 22, corresponding to the acceleration of the oscillator 2 supplied from the piezoelectric sensor 14 and a temperature signal 24 of the measured sample liquid 4 from the temperature sensor 3. The output signal from the probe 1 is transmitted to the main unit 100 via the cable 7. The signal processing unit 6 calculates a viscosity η and a density ρ with using the driving signal voltage 25, the acceleration signal 22, the temperature signal 24 if necessary and the data stored in the storage unit 6-1. The details of the signal processing unit 6 are described later.

The following data are pre-stored in the storage unit 6-1.
a driving signal frequency: $f_A$
a driving signal amplitude: $A_0$
a phase difference between the driving signal and the acceleration signal in the condition of no immersion to the sample fluid (in the air): $θ_A$
an amplitude ratio of the driving signal and the acceleration signal in the condition of no immersion to the sample fluid (in the air): $|F_A|$
a correction function that has been adjusted in advance using a reference fluid
a sonic velocity of the sample fluid: $u_0$
output data The signal processing unit 6 is connected to an external connection terminal 21 of the main unit 100. The signal processing unit 6 is able to change the above-described data from the external device 20 such as a personal computer via the external device connection terminal 21.

The driving signal frequency $f_A$ and the driving signal amplitude $A_0$ are defined to be a frequency and an amplitude generated when the oscillator 2 resonates in the condition where the oscillator 2 is not immersed to the sample fluid 4 (in the air).

The above-described driving signal 23 is a sinusoidal wave. The driving signal frequency $f_A$ and the driving signal amplitude $A_0$ are pre-stored in the storage unit 6-1. It is noted that the oscillation frequency may be swept to search the resonance frequency for every measurement, and the data of the frequency or the amplitude of the driving signal in the storage unit may be updated. In this example, the driving signal frequency $f_A$ and the driving signal amplitude $A_0$ are defined to be the frequency and the amplitude when the oscillator 2 resonates under the condition where it is not immersed to the sample fluid 4 (in the air). In the embodiment of this invention, however, it is not necessary to limit the conditions of the frequency and the amplitude to the resonance, though the sensitivity may decrease.

An immersion selection switch 18 switches the operation mode of the apparatus between the condition that the oscillator 2 is not immersed in the sample fluid 4 (in the air) and the condition that the oscillator 2 is immersed in the sample fluid.

A calibration/measurement selection switch 19 switches the calibration mode to and from the measurement mode described later. A temperature detection unit 6-10 detects the temperature based on the temperature signal 24 from the temperature sensor 3.

<Initial Measurement>

Next, described will be an initial measurement of the oscillating type physical property measuring apparatus according to one embodiment of this invention. It is assumed that the driving signal frequency $f_A$, the driving signal amplitude $A_0$, and the correction function that have previously been calibrated by the calibration process described later are pre-stored in the storage unit.

Firstly, when the oscillator 2 is driven under the condition of not being immersed in the sample fluid 4 (in the air), followings are the measuring method of the phase difference $θ_A$ between the phase of the acceleration signal 22 outputted from the piezoelectric sensor 14 and the phase of the driving signal voltage 25, and of the amplitude ratio $|F_A|$ between the amplitude of the acceleration signal 22 and the amplitude of the driving signal voltage 25.

The immersion selection switch 18 is set to the operation mode of the condition that the oscillator 2 is not immersed in the sample fluid 4 (immersion OFF). The calibration/measurement selection switch 19 is set to the measurement mode.

The driving signal 23 is generated by the driving signal generation unit 51, current flows in the coil 11, and the oscillator 2 and the support part 12 oscillate. In one embodiment of this invention, the oscillator 2 exhibits a single harmonic oscillation in the direction of the center axis of the suspension rod 10. With respect to the acceleration signal 22 from the piezoelectric sensor 14 and the driving signal voltage 25, the component of the driving signal frequency $f_A$ is extracted by a driving signal frequency component extraction unit 6-4 of the signal processing unit 6. The driving signal frequency component extraction unit 6-4 outputs the amplitude and the phase of the acceleration signal 22 and the amplitude and the phase of the driving signal voltage 25. This extraction process may be done with using the FFT (Fast Fourier Transform) or the band pass filter. It is noted that, at this time, the driving signal frequency $f_A$ is picked up from the storage unit 6-1. An input/output phase difference and amplitude ratio calculation unit 6-5, a phase difference calculation unit 6-6, and an amplitude ratio calculation unit 6-7 are set to the immersion OFF (in the air) condition by the control unit 6-2.

Under the immersion OFF condition, the input/output phase difference and amplitude ratio calculation unit 6-5 calculates the phase difference $θ_A$ and the amplitude ratio $|F_A|$ between the acceleration signal 22 and the driving signal 23 and stores them in the storage unit 6-1. The initial measurement is not always necessary for every operation. Once the phase difference $θ_A$ and the amplitude ratio $|F_A|$ are stored in the storage unit 6-1, those data can be used.

In the above-described embodiment of this invention, the calculation is made using the amplitude of the acceleration signal 22. However, the same result is derived by the calculation using the velocity or the amplitude of the displacement. Further, under the immersion OFF condition, the phase difference calculation unit 6-6 and the amplitude ratio calculation unit 6-7 are not operated.

<Measurement>

Next, the actual measuring procedure for deriving the viscosity and the density of the sample fluid is described. Firstly, the immersion selection switch 18 is set to the operation mode for the condition that the oscillator 2 is immersed in the sample fluid 4 (the immersion ON) and the oscillator 2 is immersed in the sample fluid 4.

Similarly to the initial setting, the oscillator 2 is oscillated in the sample fluid 4 by the same driving signal 23 as in the air. The frequency component of the driving signal frequency $f_A$ is extracted from the acceleration signal 22 by the driving signal frequency component extraction unit 6-4. The phase difference $θ_L$ and the amplitude ratio $|F_L|$ between the acceleration signal 22 and the driving signal voltage 25 are calculated by the input/output phase difference and amplitude ratio calculation unit 6-5.

The input/output phase difference and amplitude ratio calculation unit 6-5, the phase difference calculation unit 6-6, and the amplitude ratio calculation unit 6-7 are set to the immersion ON condition by the control unit 6-2. In the immersion ON condition, the input/output phase difference and amplitude ratio calculation unit 6-5 outputs the calculated phase difference $\theta_L$ to the phase difference calculation unit 6-6 and the amplitude ratio $|F_L|$ to the amplitude ratio calculation unit 6-7.

Under the immersion ON condition, the phase difference calculation unit 6-6 calculates a phase difference $\gamma$ that is the difference between the phase difference $\theta_L$ calculated by the input/output phase difference and amplitude ratio calculation unit 6-5 and the phase difference $\theta_A$ stored in the storage unit 6-1.

$$\gamma = \theta_A - \theta_L \tag{1}$$

The above mentioned phase difference $\gamma$ is a phase difference between the output signals of the piezoelectric sensor 14 in the air and that in the sample fluid 4.

Further, under the immersion ON condition, the amplitude ratio calculation unit 6-7 calculates an amplitude ratio $\alpha$ that is a ratio of the amplitude ratio $|F_L|$ calculated by the input/output phase difference and amplitude ratio calculation unit 6-5 to the amplitude ratio $|F_A|$ stored in the storage unit 6-1.

$$\alpha = |F_A|/|F_L| \tag{2}$$

This amplitude ratio $\alpha$ is an amplitude ratio of the output signals of the piezoelectric sensor 14 in the air to that in the sample fluid 4.

A viscosity and density calculation unit 6-8 calculates the viscosity $\eta$ and the density $\rho$ of the sample fluid 4 from the phase difference $\gamma$ calculated by the phase difference output unit 6-6, the amplitude ratio $\alpha$ calculated by the amplitude ratio calculation unit 6-7, the temperature if necessary, and the correction function stored in the storage unit 6-1 (the calculation process is described later).

An output unit 6-9 (a) displays the viscosity $\eta$, the density $\rho$ and the temperature on the screen, (b) prints them, or (c) outputs them to the external device. Alternatively, the output unit 6-9 can combine (a) to (c). They may be stored in the storage unit 6-1 as the output data.

Further, the output unit 6-9 calculates a kinematic viscosity ($=\eta/\rho$) or the product of the viscosity and the density ($=\eta \times \rho$). Furthermore, it picks up the sonic velocity data of the sample fluid 4 from the storage unit 6-1 and calculates the volume elasticity (=the square of the sonic velocity×the density) or the compressibility (=1/the volume elasticity) of the temperature outputted from the temperature signal 24. It is then outputted or stored them similarly to the viscosity $\eta$ or the density $\rho$.

<Modification>

In the above-mentioned description, the signal processing unit 6 is arranged in the main unit 100 and connected to the probe 1 by the cable 7. However, it is available to arrange power supply means such as a battery and a data transceiver (send and receive) unit such as a radio unit in the probe and for connecting wirelessly between the probe 1 and the main unit 100. Furthermore, the main unit 100 may be arranged in the probe 1.

The signal processing unit 6 can be set to the personal computer and the like, and the main unit 100 can be configured with the personal computer and the like. Further, while the temperature sensor 3 is arranged to the probe 1 as temperature measurement of the sample fluid 4, the temperature of the sample fluid 4 may be separately measured by the thermometer and be inputted as the data.

<Calibration>

Next, the calibration process of the oscillating type physical property measuring apparatus according to one embodiment of this invention is described. First, the calibration/measurement selection switch 19 is set to the calibration mode. The resonance frequency is measured with sweeping the frequency of the driving signal 23 by a predetermined amplitude in the condition where the oscillator 2 is not immersed in the sample fluid 4 (in the air). Then, this resonance frequency and the amplitude are stored in the storage unit 6-1 as the driving signal frequency $f_A$ and the driving signal amplitude $A_0$.

At least two types of reference liquid whose viscosity or density is already known are used as the sample fluid 4. The viscosity or the density is stored in the storage unit 6-1.

The same operation in the initial measurement and in the measurement described above is made. A correction coefficient S (a complex number) is derived in order that the measured viscosity $\eta$ and density $\rho$ of the reference liquid are equal to the specified viscosity and density of the reference liquid. The correction function is determined based on the correction coefficient S of plural types of the reference liquids. It is noted that the process of calculating the correction coefficient is described later.

Under the calibration mode, the viscosity and density calculation unit 6-8 picks up the viscosity and the density of the reference liquid from the storage unit 6-1 and calculates the correction equation to store it in the storage unit 6-1.

<Viscosity and Density Calculation>

Figure 5:
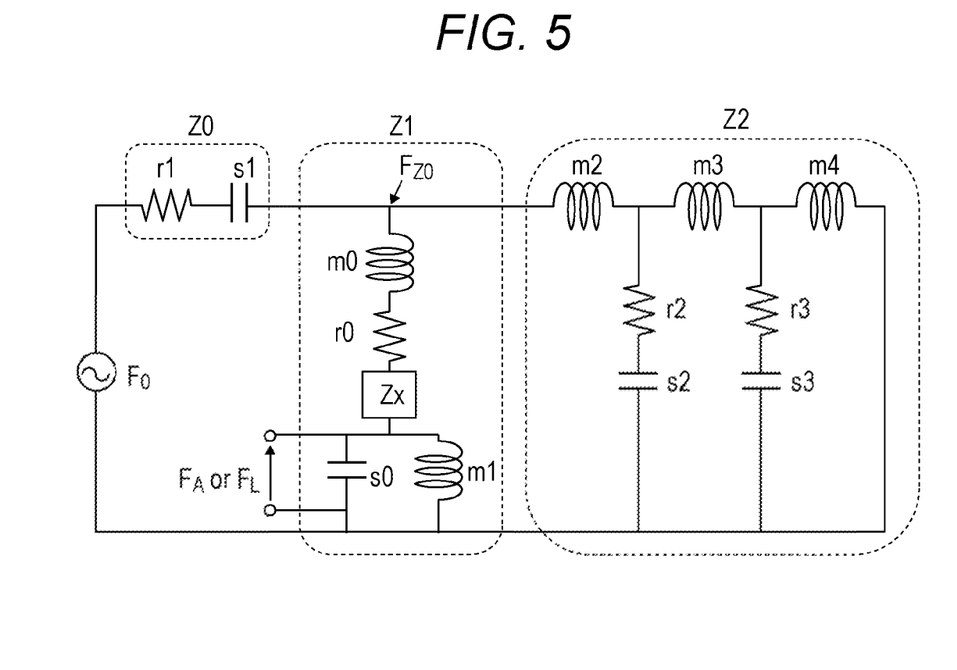
FIG. 5 is an electrical equivalent circuit diagram of a probe mechanical system of the oscillating type physical property measuring apparatus according to one embodiment of this invention.

The process of calculating the viscosity and the density is described below. First, the probe mechanical system is described with the equivalent electric circuit as seen in FIG. 5. Respective impedances are defined for three areas of the equivalent circuit, which are called as $Z_0$, $Z_1$, and $Z_2$, respectively. Specifically, the impedance Z of the entire circuit referred from the driving force $F_0$ side can be recognized as which the parallel circuits of $Z_1$ and $Z_2$ are connected in series to the $Z_0$. $Z_x$ represents the mechanical impedance of the sample fluid. Further, $F_{Z0}$ represents the voltage which the power supply voltage equivalent to the driving force $F_0$ is the point where the voltage is dropped by $Z_0$. With respect to the $Z_1$, the impedance changes before and after the probe contacts with the sample fluid. Thus, the $Z_1$ before the probe contacts with the sample fluid is represented as $Z_{1A}$, and the $Z_1$ after the probe contacts with the sample fluid is represented as $Z_{1L}$. It is noted that the driving force $F_0$ is proportional to the current of the driving signal.

First, the case where the probe is put in the air is considered.

$F_{Z0}$ in the air is represented as $F_{Z0A}$, and the $F_{Z0A}$ is described as follows.

$$F_{Z0A} = \frac{F_0}{1 + \left(\frac{1}{Z_{1A}} + \frac{1}{Z_2}\right)Z_0} \tag{3}$$

The $s_0$ represents the stiffness of the piezoelectric element and is sufficient to meet $\omega m_1 \ll s_0/\omega$. Therefore, when the oscillator is in the air, assuming that the force corresponding to the acceleration detected by the piezoelectric element is the $F_A$, the following formula is obtained.

$$F_A = \frac{j\omega m_1}{Z_{1A}} F_{Z0A} \quad (4)$$

Next, the case where the oscillator is in the sample fluid will be considered.

The following formula can be described, where $F_{Z0L}$ represents the $F_{Z0}$ after the contact.

$$F_{Z0L} = \frac{F_0}{1 + \left(\frac{1}{Z_{1L}} + \frac{1}{Z_2}\right) Z_0} \quad (5)$$

Taking into consideration of the mechanical impedance $Z_x$ of the sample fluid, the $Z_{1L}$ can be described as follows.

$$Z_{1L} = Z_{1A} + Z_x \quad (6)$$

$F_L$ represents the force corresponding to the acceleration detected by the piezoelectric element after the oscillator contacts with the sample fluid, and the following formula is obtained.

$$F_L = \frac{j\omega m_1}{Z_{1L}} F_{Z0L} \quad (7)$$

Therefore, provided that the driving force $F_0$ can be obtained previously, the mechanical impedance $Z_x$ can be derived. Because of deriving the mechanical impedance $Z_x$ without using the driving force $F_0$, it is treated with taking the ratio of the $F_L$ and the $F_A$ detected before and after the oscillator contacts with the sample fluid. So the following formulas are obtained.

$$Z_x = \left(\frac{F_A}{F_L} - 1\right) \cdot Z_p \quad (8)$$

$$Z_p = Z_{1A} + \frac{1}{\frac{1}{Z_0} + \frac{1}{Z_2}} \quad (9)$$

The mechanical impedance Zp is a constant determined by the mechanism of the probe including the oscillator and the oscillation frequency. Therefore, it is indicated that the mechanical impedance $Z_x$ of the sample fluid can be calculated from the acceleration information detected by the piezoelectric element before and after the contact with the sample fluid. Further, Zp is an amount that depends only on the oscillation frequency ω and the probe mechanism including the part by which the probe is held in the measurement. Strictly, the Zp depends also on the temperature. It is not easy to derive Zp for the probe accurately from the formula (9). Provided that, however, the $Z_x$ is already known, Zp can be derived from the formula (8).

For example, it is assumed that the $Z_x$ is a known mass m and the $F_A$ represents the force corresponding to the acceleration detected by the piezoelectric element under no load condition in the air. It is then assumed that the $F_L$ represents the force corresponding to the acceleration detected by the piezoelectric element when the mass m is set to the oscillator in the air. With the substitution of these values in the formula (8), Zp can be derived. It is noted that $F_A$, $F_L$, and Zp are complex numbers.

Here, provided that the derived Zp is as follows, $$Zp = |Zp| \cdot e^{j\theta_p}$$

$Z_x$ results in the followings based on the formula (1) and the formula (2).

$$Zx = |Zx| \cdot e^{j\theta_p} \quad (10)$$

$$|Zx| = \sqrt{\alpha^2 - 2\alpha \cdot \cos\gamma + 1} \cdot |Zp|$$

$$\theta_x = \tan^{-1}\left(\frac{\alpha(\tan\theta_p \cdot \cos\gamma + \sin\gamma) - \tan\theta_p}{\alpha(\cos\gamma - \tan\theta_p \cdot \sin\gamma) - 1}\right)$$

As set forth, with obtaining Zp in advance, the mechanical impedance of the sample fluid can be derived with the amplitude ratio α and the phase difference γ. Further, with obtaining Zp in advance in a proper frequency range, $Z_x$ can be derived not only limited with the resonance frequency but also with the frequency range. Furthermore, with obtaining Zp in advance in a proper temperature range, $Z_x$ can be derived in that temperature range.

In the above process of calculating $Z_x$, the forces $F_A$ and $F_L$ detected by the piezoelectric element before and after the contact to the sample fluid are measured and derived for the constant driving force $F_0$. However, the $Z_x$ can be derived also by changing the driving force $F_0$ to make the forces $F_A$ and $F_L$ detected by the piezoelectric element before and after the contact to the sample fluid constant and by measuring the driving force $F_0$ before and after the contact to the sample fluid. Provided that the $F_{0A}$ represents the driving force $F_0$ before the probe contacts with the sample fluid and $F_{0L}$ represents $F_0$ after the contact, $Z_x$ can be calculated from $Z_x = (F_{0L}/F_{0A} - 1) \times Zp$.

Furthermore, $Z_x$ of the formula (10) includes the influence by the fluid around the suspension rod part of the oscillator. Thus, this is corrected to calculate the mechanical impedance of the sample fluid when the oscillator end part only oscillated. It is assumed that $Z_T$ represents the mechanical impedance of the sample fluid in the case the spherical part of the oscillator end part had no rod part of the suspension rod. $Z_T$ is derived by multiplying the correction coefficient S (a complex number) by $Z_x$ as follows.

$$S = |S| e^{j\theta_x} \quad (11)$$

$$Z_T = S \cdot Zx = |S||Zx| e^{j(\theta_x + \theta_x)} = |Z_T| e^{j\theta_T} \quad (12)$$

In the driving signal frequency $f_A$, it is assumed that $Z_{2C}$ represents the mechanical impedance of the probe case 8 and the probe holder 5. Then, the spring coefficient is set in order that the stiffness s2 in the oscillation direction of the second elastic member 16 is sufficiently small (s2/ω<<ω$Z_{2c}$) and thus the influence by the change in the $Z_{2C}$ can be ignored. This allows to suppress the influence from the change in the holding condition.

Next, it calculates the theoretical values of the viscosity and the density of the fluid using the rigid body sphere model that oscillates in the static fluid.

A model which the rigid body sphere of a radius R oscillates with a constant angular frequency ω and an amplitude $u_0$ in a non-compressed viscous fluid having the viscosity η and the density ρ is assumed.

The resistance F that the oscillating sphere receives from the viscous fluid can be obtained by the following formula (Reference: Fluid Mechanics 2nd Edition, Landau and Lifshitz Course of Theoretical Physics volume 6, L. D. Landau and E. M. Lifshitz).

$$F = 6\pi R\eta u\left(1 + \frac{R}{\delta}\right) + j\omega 3\pi R^2 u \sqrt{\frac{2\eta\rho}{\omega}} \left(1 + \frac{2R}{9\delta}\right) \qquad (13)$$

In the above reference, the F is defined as the resistance. In practice, the F is the power (affecting force) to the fluid. Further, δ in the formula is written as follows.

$$\delta = \sqrt{(2\eta/\omega\rho)}$$

The mechanical impedance $Z_T$ of the fluid can be derived, provided that both sides of the formula (13) that is the formula of the power (affecting force) to the viscous fluid are divided by the velocity u, and the following formula is derived.

$$Z_T = \frac{F}{u} = 6\pi R\eta\left(1 + \frac{R}{\delta}\right) + j\omega 3\pi R^2 \sqrt{\frac{2\eta\rho}{\omega}} \left(1 + \frac{2R}{9\delta}\right) \qquad (14)$$

The real number part and the imaginary number part of Z include the viscosity η and the density ρ, respectively, and they are unknown values. On the other hand, the oscillation angular frequency ω and the radius R of the sphere are known values. Further, the real number part and the imaginary number part of $Z_T$ are the values that can be measured based on the formula (12). Therefore, with respect to the unknown values η and ρ, it can be solved with simultaneous equation for the real number part and the imaginary number part.

That is, the viscosity η and the density ρ are derived as follows based on the formula (12) and the formula (14).

$$\eta = \frac{2|Z_r|\sin\theta_r}{27\pi R}\left[\frac{9}{28}\frac{Y}{\tan\theta_r} + \left(\frac{7}{9}\tan\theta_r\right)\frac{1}{Y} - 1\right] \qquad (15)$$

$$\rho = \frac{27|Z_r|\cos\theta_r}{28\pi R^3 \omega} \qquad (16)$$

$$Y = \left(\frac{5}{9}\tan\theta_r - 1\right) \pm \sqrt{1 + (\tan\theta_r)^2 - \frac{10}{9}\tan\theta_r} \quad (Y > 0) \qquad (17)$$

Following description is for the correction function. First, the mechanical impedance $Z_x$ of the reference liquid including the influence of the suspension rod 10 is calculated by the formula (10). Next, the mechanical impedance $Z_T$ is derived by the formula (14) with the known viscosity and density of the reference liquid. The $Z_x$ and the $Z_T$ are substituted in the formula (12) to derive |S| and $\theta_S$ of the correction coefficient S. The correction coefficient S is derived for multiple types of the reference liquid whose mechanical impedance is within a predetermined range. The correction function for any mechanical impedance $Z_x$ can be derived with such procedure. The correction function is a function of the mechanical impedance. With the correction function being stored in the storage unit 6-1 at the factory shipment, the correction coefficient S according to $Z_x$ resulted from the formula (10) can be derived. Thus, the corrected mechanical impedance $Z_T$ can be calculated.

As the details are described in this section, this embodiment allows for the measurement of the viscosity and the density of the sample fluid separately and simultaneously. Therefore, the oscillating type physical property measuring apparatus of this invention can be used not only as the viscometer for the fluid such as liquid, but also as the density meter or the kinematic viscometer, or further as the hydrometer.

INDUSTRIAL APPLICABILITY

The oscillating type physical property measuring apparatus according to this invention can be used not only as the viscometer for the fluid but also as the density meter or the kinematic viscometer. Furthermore, the ratio of volume elasticity or of compressibility of the sample fluid can be measured, provided that the sonic velocity of the sample fluid can be obtained previously. Therefore, this invention is available and applicable for wide range of industrial fields.

DESCRIPTION OF REFERENCE SIGNS

1 Probe
2 Oscillator
3 Temperature sensor
4 Sample fluid
5 Probe holder
6 Signal processing unit
7 Cable
8 Probe case
9 Oscillator end part
10 Suspension rod
11 Coil
12 Elastic member connecting part
13 Magnet
14 Piezoelectric sensor
15 Piezoelectric sensor mass
16 Second elastic member
17 First elastic member
18 Immersion selection switch
19 Calibration/measurement selection switch
20 External device
21 External device connection terminal
22 Acceleration signal
23 Driving signal
24 Temperature signal
25 Driving signal voltage
40 Yoke
41 Elastic member
50 Control unit
51 Driving signal generation unit
100 Main unit
F0 Driving force of the driving unit
m0 Mass of the oscillator (except m1)
m1 Mass of the piezoelectric sensor mass
m2 Mass of the elastic connecting part
m3 Mass of the case
m4 Mass of the probe holder
r0 Mechanical resistance to the oscillator
r1 Mechanical resistance of the first elastic member
r2 Mechanical resistance of the second elastic member
r3 Mechanical resistance between the case and the probe holder
s0 Stiffness of the piezoelectric sensor
s1 Stiffness of the first elastic member
s2 Stiffness of the second elastic member
s3 Stiffness of the probe holder
Z0, Z1, Z2 Mechanical impedance of Oscillator for each area
Zx Mechanical impedance of the sample fluid

The invention claimed is:
1. An oscillating type physical property measuring apparatus equipped with an oscillator,
wherein an end part of the oscillator is shaped as a sphere, the oscillating type physical property measuring apparatus comprising:
the oscillator;
an oscillation driving unit adapted to cause the oscillator to oscillate;
a probe including a sensor for detecting acceleration of the oscillator;
a driving signal output unit adapted to output a driving signal to the oscillation driving unit so that driving forces when the end part respectively oscillates in the air and in a fluid-correspond to predetermined values; and calculation means for calculating a viscosity and/or a density of the fluid, based on a predefined mechanical impedance of the probe including the oscillator and on an amplitude ratio and a phase difference of accelerations detected by the sensor when the end part respectively oscillates in the air and in the fluid.

2. An oscillating type physical property measuring apparatus equipped with an oscillator, wherein an end part of the oscillator is shaped as a sphere, the oscillating type physical property measuring apparatus comprising:

the oscillator;

an oscillation driving unit adapted to cause the oscillator to oscillate;

a probe including a sensor for detecting acceleration of the oscillator;

a driving signal output unit adapted to output a driving signal to the oscillation driving unit so that accelerations detected by the sensor when the end part respectively oscillates in the air and in a fluid correspond to predetermined values; and calculation means for calculating a viscosity and/or a density of the fluid, based on a predefined mechanical impedance of the probe including the oscillator and on an amplitude ratio and a phase difference of a driving signal when the end part respectively oscillates in the air and in the fluid.

3. The oscillating type physical property measuring apparatus according to claim 1, wherein a velocity or a displacement is used in place of the acceleration.

4. The oscillating type physical property measuring apparatus according to claim 1, wherein a shape of the end part of the oscillator is a shape whose resistance by a fluid is logically derived.

5. The oscillating type physical property measuring apparatus according to claim 1, further comprising means for correcting an influence by a resistance of the fluid affected to a suspension rod supporting the end part of the oscillator.

6. The oscillating type physical property measuring apparatus according to claim 1, wherein the oscillator is coupled to a support part by a first elastic member, and the support part and a probe case are coupled by a second elastic member, and a stiffness of the second elastic member in an oscillation direction is sufficiently small so that an influence from a change of a mechanical impedance of the probe case and/or a probe holder is ignored.

7. The oscillating type physical property measuring apparatus according to claim 2, wherein a velocity or a displacement is used in place of the acceleration.

8. The oscillating type physical property measuring apparatus according to claim 2, wherein a shape of the end part of the oscillator is a shape whose resistance by a fluid is logically derived.

9. The oscillating type physical property measuring apparatus according to claim 2 further comprising means for correcting an influence by a resistance of the fluid affected to a suspension rod supporting the end part of the oscillator.

10. The oscillating type physical property measuring apparatus according to claim 2, wherein the oscillator is coupled to a support part by a first elastic member, and the support part and a probe case are coupled by a second elastic member, and a stiffness of the second elastic member in an oscillation direction is sufficiently small so that an influence from a change of a mechanical impedance of the probe case and/or a probe holder is ignored.

* * * * *